United States Patent [19]
Shimizu et al.

[11] Patent Number: 5,609,819
[45] Date of Patent: Mar. 11, 1997

[54] METHOD OF STERILIZING SEALED VIAL AND APPARATUS FOR SEALING THE VIAL

[75] Inventors: Katsumi Shimizu; Washiro Honda, both of Honjo, Japan

[73] Assignee: Eisai Co., Ltd., Tokyo, Japan

[21] Appl. No.: 499,658

[22] Filed: Jul. 7, 1995

[30]  Foreign Application Priority Data

Jul. 12, 1994 [JP] Japan .................................. 6-160013

[51] Int. Cl.⁶ .............................. A61L 2/12; A61L 2/24; B65B 55/02; B65B 55/14
[52] U.S. Cl. .................................. 422/3; 422/21; 422/22; 422/303; 422/304; 250/455.11; 53/425
[58] Field of Search .................................. 422/3, 21, 22, 422/300, 302, 303, 304, 308; 53/425; 250/455.11

[56]  References Cited

U.S. PATENT DOCUMENTS

| | | | |
|---|---|---|---|
| 3,674,422 | 7/1972 | Gray | 422/21 |
| 3,737,608 | 6/1973 | Nagao et al. | 422/21 |
| 3,880,586 | 4/1975 | Murayama et al. | 422/21 |
| 3,885,915 | 5/1975 | Utsumi et al. | 422/21 |
| 5,132,504 | 7/1992 | Iijima et al. | 422/21 |

Primary Examiner—Robert J. Warden
Assistant Examiner—E. Leigh Dawson
Attorney, Agent, or Firm—Griffin, Butler, Whisenhunt & Kurtossy

[57]  ABSTRACT

While a sealed vessel such as a vial having an inside plug such as a rubber stopper is conveyed, the sealed vessel is slanted by a slanting device until liquid medicine in the sealed vessel touches the inside plug. The sealed vessel is moved and simultaneously rotated by a rotating device while the vial is slanted. The liquid medicine in the sealed vessel is heated at a heating portion by heat energy such as infrared, fuel gas and microwave, so that the heated liquid medicine causes heat sterilization of the whole sealed vessel including the inside plug. Sterilization can be completely carried out by providing a heat-retaining portion, cooling portion and drying portion next to the heating portion. An infrared radiation thermometer is provided at the end of the heating portion to measure the temperature of the liquid medicine, so that the temperature of the liquid medicine in each sealed vessel may be controlled to a desired temperature.

18 Claims, 6 Drawing Sheets

METHOD OF STERILIZING SEALED VIAL AND APPARATUS FOR SEALING THE VIAL

BACKGROUND OF THE INVENTION

1. Field of the Invention

The present invention relates to a method of consecutively carrying out heat sterilization of a sealed vessel such as a vial having an inside plug such as a rubber stopper and containing a liquid medicine and to an apparatus for carrying out the method.

2. Description of the Related Art

Conventionally, sterilization treatment of a vial containing a liquid medicine such as injection material has been conducted in the process of producing the filled vial. A method of steam sterilization using a high-pressure steam tank is well known as the above method. However, the above method of steam sterilization is a batch process which has not been associated with the filling process and it has not been able to immediately measure a temperature of each vial.

Consequently, each vial has not been independently detected as to whether the sterilization is completely carried out and a guarantee for the sterilization of each vial has depended on the condition of the whole batch.

Furthermore, a sealed vessel having an inside plug such as the rubber stopper does not allow measurement of the temperature of the inside plug, so that it has been difficult to guarantee that such a vial is sterilized.

However, in the method of sterilizing consecutively the sealed vessel such as the vial having the inside plug such as the rubber stopper, the inside plug should be sterilized to the same degree as the liquid medicine.

Also, heating from the outside of the vial by using a hot air as in a conventional consecutive sterilizer has not heated the vial sufficiently uniformly to completely sterilize the vial because of a usual aluminum-cap or a resin flip-cap covering the inside plug. The resin flip-cap may be destroyed by the hot air.

SUMMARY OF THE INVENTION

The purposes of the present invention are met by solving the aforesaid art disadvantages and by providing a sterilizing apparatus and method capable of sequentially carrying out heat sterilization of a sealed vessel, such as a vial, having an inside plug and liquid medicine held therein in a short time and with a relatively simple apparatus.

The method for achieving the purposes of the present invention will be illustrated below.

The sterilization method of the sealed vessel, such as the vial, having the inside plug, such as a rubber stopper, during sequential conveying of the sealed vessels is characterized by moving the sealed vessels while slanting each sealed vessel until the liquid medicine in the sealed vessel touches the inside plug and rotating the sealed vessel, heating the liquid medicine in the sealed vessel by heat energy such as an infrared line heater, gas heating and microwave heating, and carrying out heat sterilization of the whole sealed vessel including the inside plug by means of the heated liquid medicine.

In the aforesaid method, it is advisable that the sealed vessel should remain for a certain period of time after reaching the predetermined temperature by heating, and that the sealed vessel should be cooled and dried after remaining at the predetermined temperature for a certain period of time.

Sterilization can be assured by measuring the temperature of the liquid medicine in each sealed vessel by an infrared radiation thermometer after the temperature of the sealed vessel reaches the predetermined temperature, automatically controlling the operating condition of the infrared heater, gas heating or microwave heating corresponding to the changing temperature, and defining a heating temperature of the liquid medicine of each sealed vessel.

Apparatus for achieving the purposes of the present invention will be illustrated below.

A sterilization apparatus for sterilization treatment of the sealed vessel, such as the vial, having the inside plug, such as a rubber stopper, during sequential conveying of sealed vessels is comprised of a device which causes the sealed vessel to slant until the liquid medicine touches the inside plug during the conveying process, a device which causes the sealed vessel to move and simultaneously rotate while being slanted, and a heating device such as the infrared line heater, gas heating and microwave heating to heat the liquid medicine in the sealed vessel while being slanted.

More effective sterilization can be obtained when the sterilizing apparatus includes a heat-retaining device such as a heater so as to maintain for a certain period of time the predetermined temperature after the sealed vessel reaches that temperature.

It is advisable that the sterilizing apparatus includes a cooling device and a drying device next to the heat-retaining device to maintain for a certain period of time the temperature after the sealed vessel reaches the predetermined temperature.

Sterilization can be assured by the sterilizing apparatus through the use of a control system to automatically control the heating condition of the sealed vessel, relative to changes in temperature of liquid medicine in each sealed vessel by measuring with an infrared radiation thermometer provided at an end of a heating portion during the conveying process in order to maintain the predetermined degree of sterilization of the liquid medicine in each sealed vessel.

Specific operation of the present invention will be illustrated below.

The consecutively moved plural vials are held at their necks by a conveyor bucket and being slanted at an inverting portion until the liquid medicine touches the inside plugs as the vials pass through a heating furnace such as an infrared radiation heating, fuel gas heating and microwave heating. The vial is rotated by an external belt or the like so that the vial is equally heated, including the inside plug.

The vial is retained in the heat-retaining portion, e.g. an infrared heater or a fuel gas heater, at the predetermined temperature after reaching that temperature so as to be completely sterilized. The sterilized vial is returned to the initial upstanding state, cooled and dried and advanced to the next process.

Effectiveness of the present invention will be illustrated below.

In the present invention, the consecutive heat sterilization of the whole sealed vessel is facilitated to equally and easily heat the temperature of the liquid medicine in the sealed vessel such as the vial having the inside plug so that the sealed vessel is rotated and heated while being slanted until the liquid medicine in the vial touches the inside plug.

Since the output of the infrared heating, fuel gas heating, microwave heating or the like is automatically controlled based on the temperature of each sealed vessel as measured by the infrared radiation thermometer provided at the exit of the heating furnace, although the temperature of the conveyed sealed vessels changes, the temperature of the consecutively conveyed sealed vessels is maintained at a certain level.

The sealed vessel heated to a peak temperature at the heating furnace exit is retained in the heat-retaining portion provided with the heater or the like for a certain period of time so as to be completely sterilized. The sterilized sealed vessel is cooled to around room-temperature during a passage through an air-cooling portion and a water-cooling portion and then is conveyed to the next process.

The aforementioned method and apparatus of the present invention carry out the heat sterilization sequentially and with reliability, even with the relative simple structure of the apparatus.

According to the method of the present invention, an autoclave will not be needed and there is the possibility of a continuous production line for processing the sealed vessels. The heat sterilization for a short time has the advantage of completely sterilizing the vessel and liquid medicine without any detrimental harm to the liquid medicine as compared with the autoclave.

BRIEF DESCRIPTION OF THE DRAWINGS

The above and other objects of the present invention will be seen by reference to the description taken in connection with the accompanying drawings, in which.

DETAILED DESCRIPTION OF THE PREFERRED EMBODIMENT(S)

Preferred embodiments of the present invention will be illustrated with the drawings.

The sealed vessel will be illustrated as a vial in the preferred embodiments. The present invention is not intended to be limited to the vial example and can be used for other vessels, such as a cartridge and syringe, that keep liquid therein.

Figure 6:
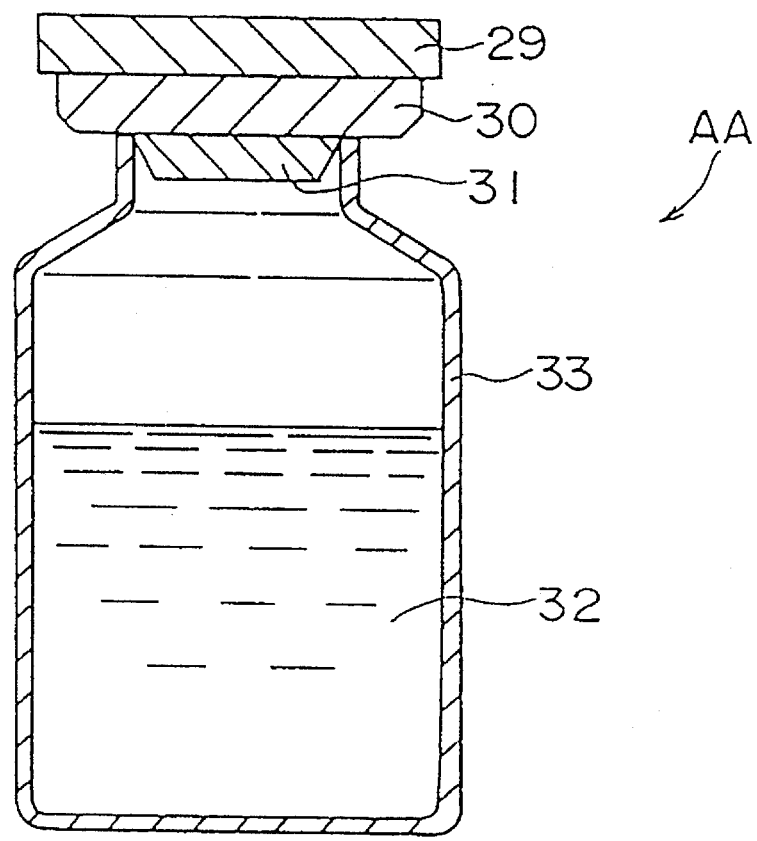
FIG. 6 is a front view of an example of the vial having an inside plug such as the rubber stopper.

FIG. 6 illustrates the vial (AA), in which a liquid medicine (32) is contained in a bottle-body (33) and the vial is sealed at its mouth with the inside plug (31) such as the rubber stopper. Numeral (30) represents an aluminum-cap and numeral (29) represents a resin flip-cap in the drawing, respectively.

A discussion concerning an apparatus for sterilizing the vial (AA) in the present invention will be set forth below.

In the apparatus of the present invention, each vial is sequentially delivered from a bucket and rotated until the liquid medicine touches the inside plug (31), e.g. rubber stopper, in the vial. The vial passes through a heating furnace such as an infrared heater, fuel gas heater and microwave heater so as to sterilize the liquid medicine in the vial and simultaneously effect heat sterilization of the whole vial including the rubber stopper in the vial by the sterilized liquid medicine.

Figure 1:
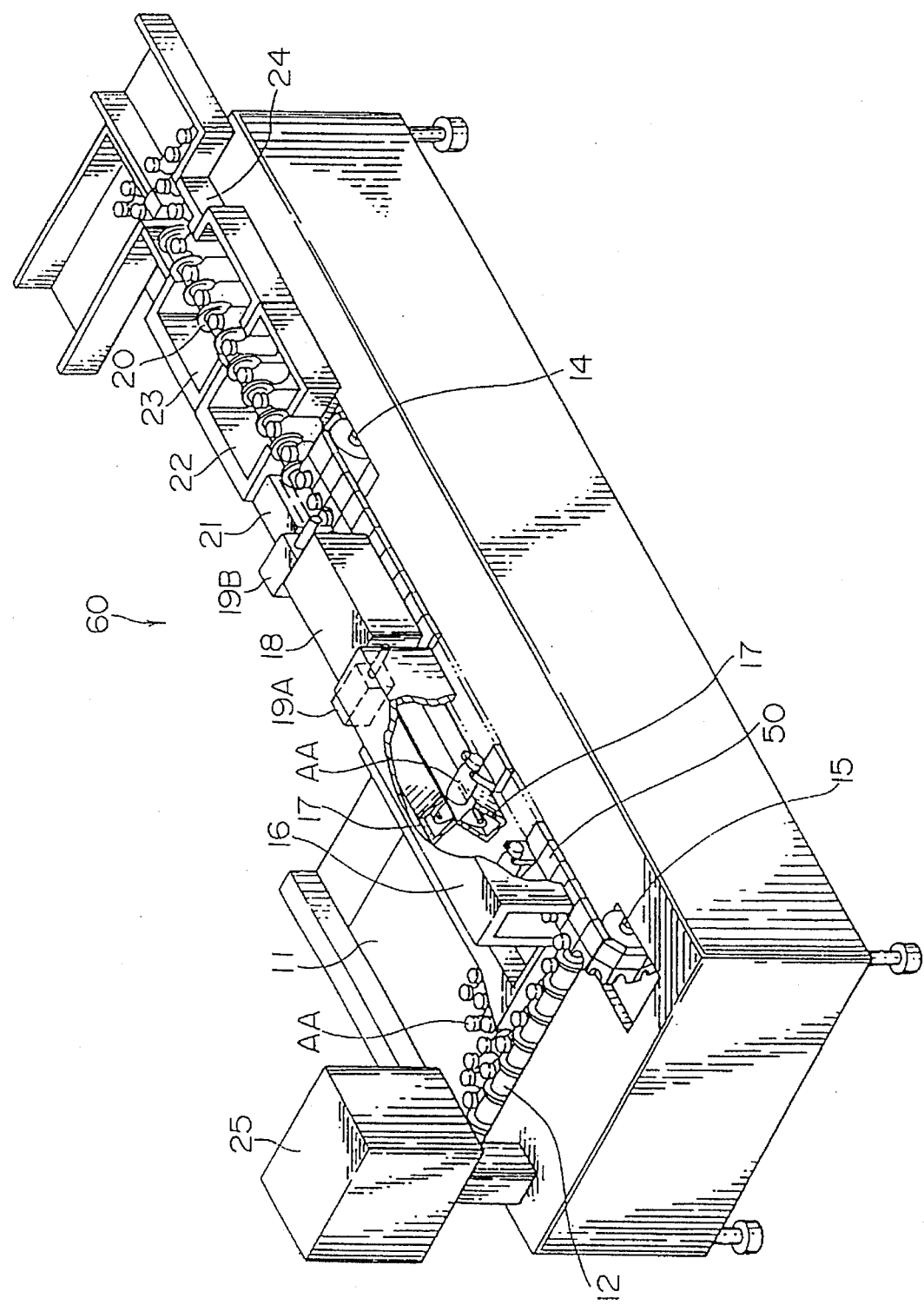
FIG. 1 is a partially cutaway view in perspective of the outline of the apparatus according to the present invention.

FIG. 1 is a perspective view of a sterilization device (60) according to the present invention as aforesaid.

The vials to be sterilized are taken out one by one from a feed hopper (11) by means of a screw (12) and delivered to a conveyor bucket (50) which delivers the vials (AA) to the inside of the sterilization device (60). The conveyor bucket (50) is mounted to an endless chain engaged to a pair of driving sprocket (14), one being shown in FIG. 1, and an interlocked sub-sprocket (15).

The conveyor bucket (50) has structure which can vary the angle of an end of the conveyor bucket, which causes the vial to be slanted until the liquid medicine reaches the inside plug (31) as soon as the vial enters the heating furnace so as to effect the heat sterilization of the vial while passing through a heating portion (16) and a heat-retaining portion (18). At the same time, the vial is rotated by an external belt.

Numerals (19A) and (19B) in the drawing are infrared radiation thermometers used to measure the temperature of the vial heated and sterilized in the heating portion (16) and the heat-retaining portion 18. The vial (AA) after being sterilized in the heating portion (16) and the heat-retaining portion (18) is delivered to an exiting screw (20) so as to be cooled during passage through an air-cooling portion (21) by cool air and a water-cooling portion (22) by cool water and then to be dried at a drying portion (23) by blown air.

The vials (AA) are sorted into inferior and superior products at a distinguishing portion (24) for distinguishing whether each of the vials (AA) reached a temperature within the predetermined temperature limits, based on signals outputted from the infrared radiation thermometers (19A) and (19B) oriented at two measuring positions. Numeral (25) represents a control system, which control system (25) has memory for and control of the whole device, for example, the setting of sterilization temperature limits for the vial, automatically controlling output from an infrared line heater (17), etc., so as to maintain temperature limits for the vial by respective measuring signals sent from infrared radiation thermometers (19A) and (19B) and distinguishing whether the sterilization was completely carried out.

Next, the heat sterilization process using the infrared line heater in the heating portion (16) will be explained.

Figure 2:
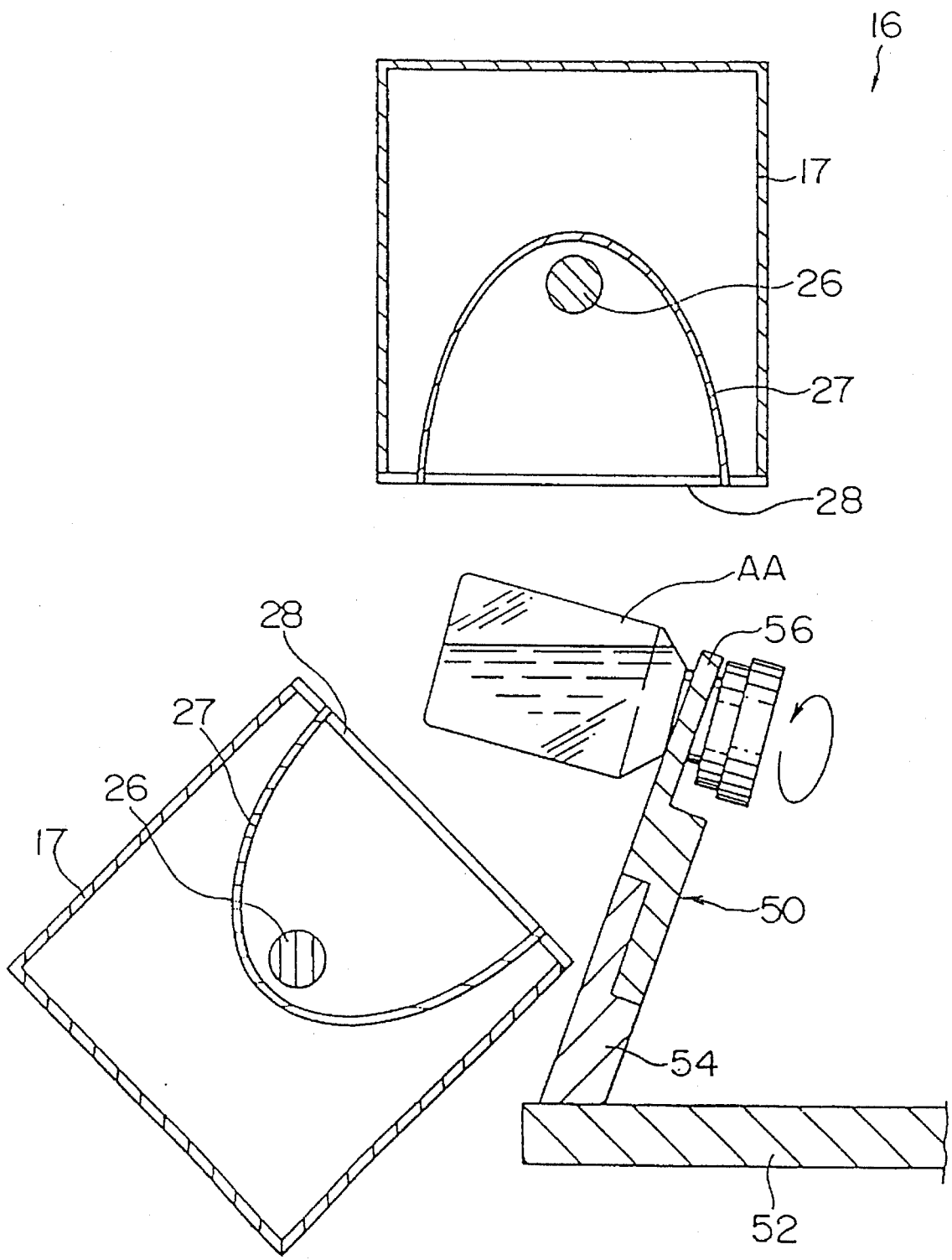
FIG. 2 is a sectional view of the inside of the heating portion

As shown in FIG. 2, the heating portion (16) heats the liquid medicine using the infrared line heater (17) directed at both upper and bottom portions of the vial or only the upper portion of the vial to heat the vial while being slanted such that the inside plug in the vial touches the liquid medicine. The liquid medicine is equally heated because the vial is heated while being rotated by a rubber belt or the like.

The infrared line heater (17) is composed of a filament-tube (26), a converging mirror (27) and a visible radiation cut-filter (28), all of which in combination effectively heat the vial.

The visible radiation cut-filter (28) is adapted to prevent eyes of a person and the liquid medicine from being damaged by strong light passing from heater portion (16).

Figure 3:
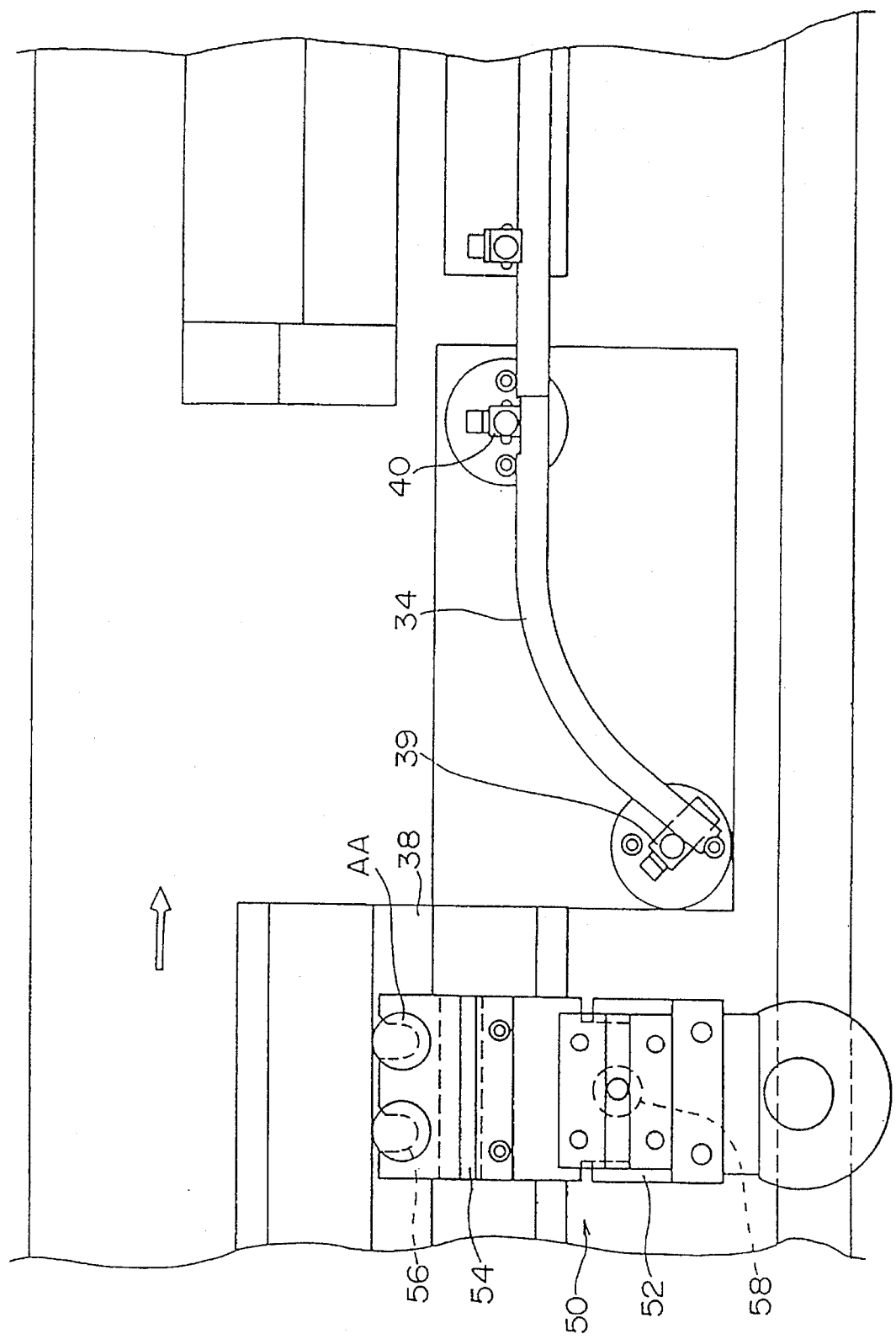
FIG. 3 is a plane view of an embodiment of the device which causes the vial to slant.
Figure 4:
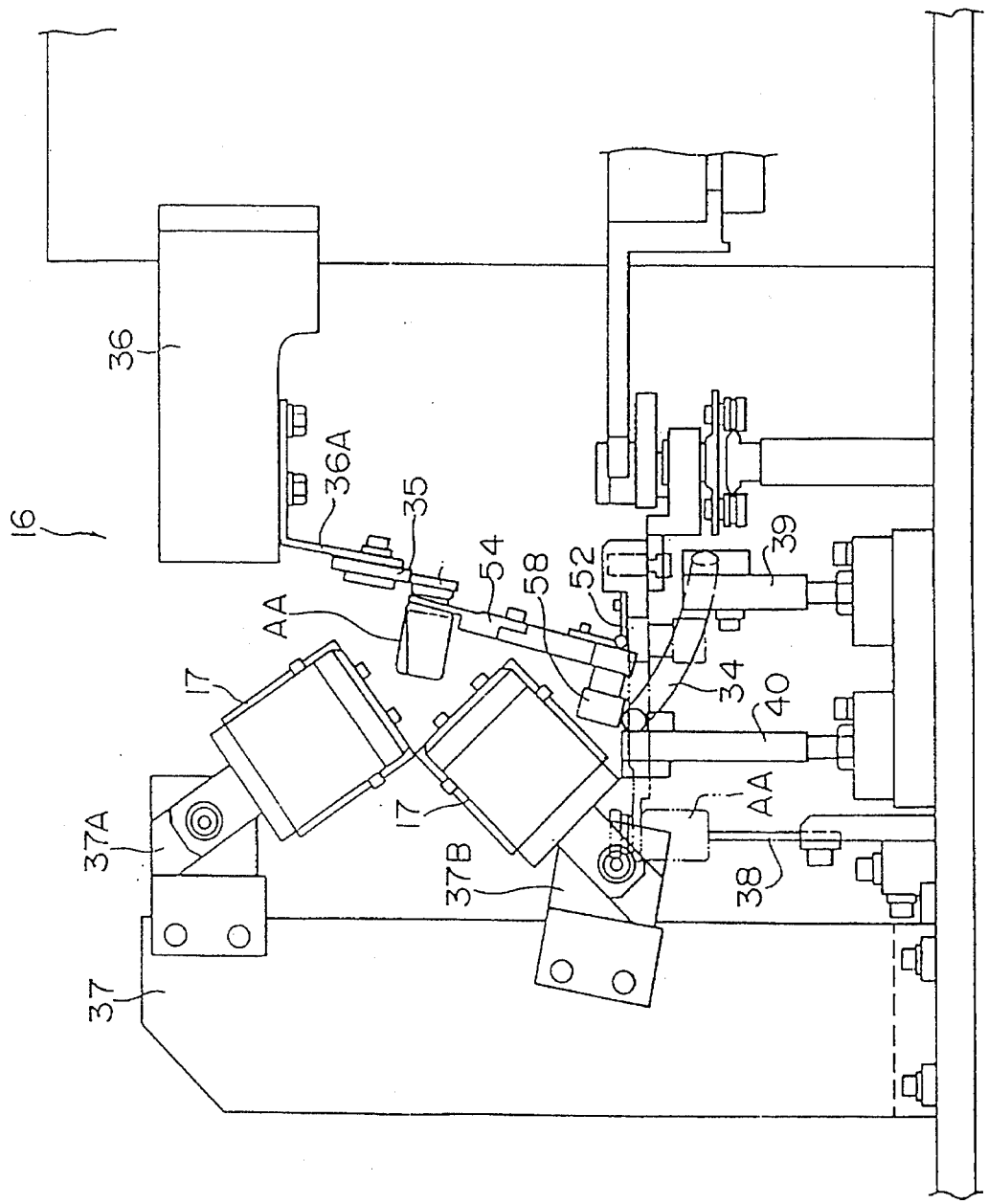
FIG. 4 is a side view of the device of FIG. 3.
Figure 5:
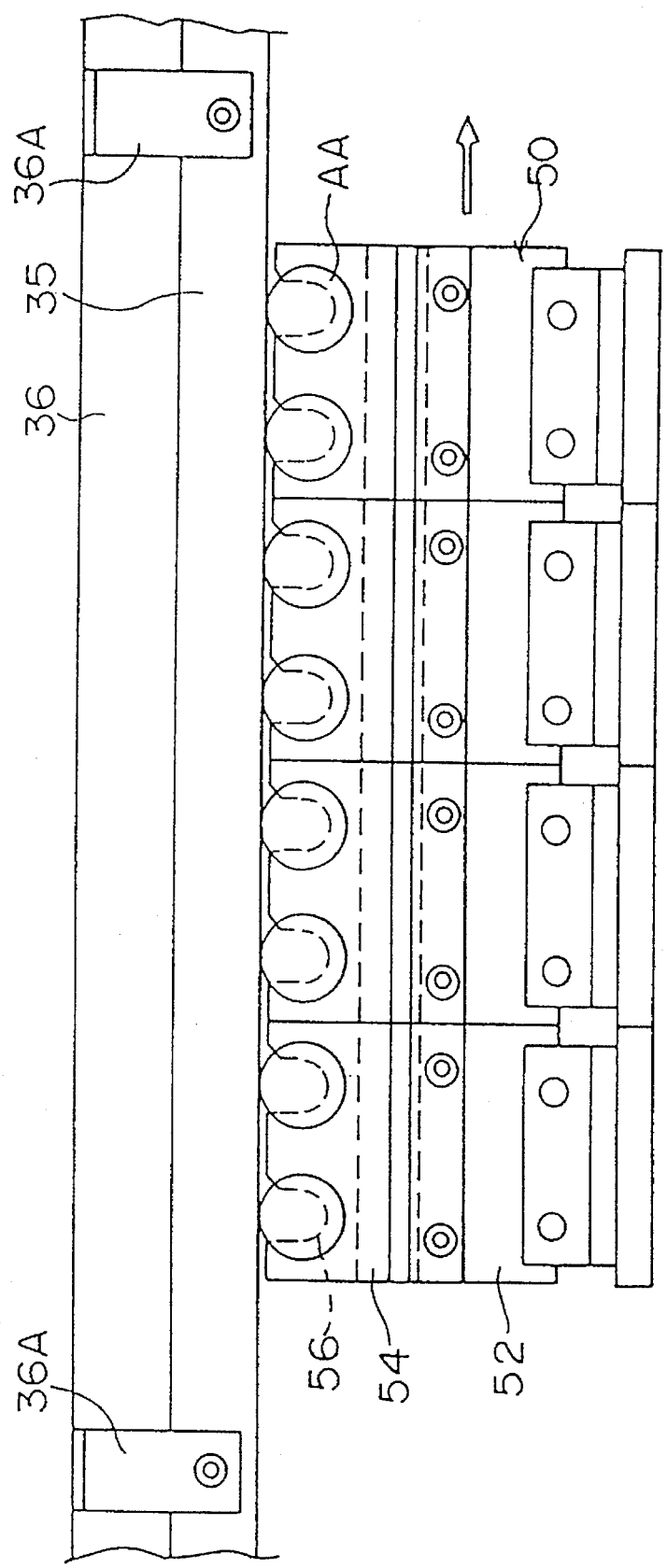
FIG. 5 is a plane view of an embodiment of the device which causes the vial to rotate.

Illustrating the aforesaid device for causing the vial to be slanted and the device for causing the vial to be rotated in the heating portion (16), FIG. 3 and FIG. 4 show the former device and FIG. 5 shows the latter device.

In FIG. 3 and FIG. 4, the conveyor bucket (50) is comprised of a horizontal portion (52) and a raisable portion

(54) movably provided thereto, which raisable portion (54) has a cap portion (56) clamping the vial (AA).

The infrared line heaters (17) are oriented at stays (37A) and (37B) provided on a frame (37) of the heating portion (16) in an upward direction and a downward direction, respectively. As the vial (AA) clamped by the cap portion (56) of the conveyor bucket (50) is conveyed on a rail (38) by the conveyor bucket (50) and then comes to a cam-rail slanting bucket (34) which a cam follower (58) provided under the raisable portion (54) of the conveyor bucket (50) is supported (34) curves in an arcing starting from the right side to the left side in FIG. 3 (a top view), namely, in an arcing state from the bottom to the top in FIG. 4 (a side elevational view), whereat the cam follower (58) advances corresponding to movement of the cam-rail slanting bucket (34) so as to cause the raisable portion (54) to rise in a hinge portion from the horizontal portion (52) as shown in FIG. 4.

That is, an inward and upward movement of the cam-rail slanting bucket (34) occurs with an advancing direction of the vial (AA) and causes the cam follower (58) provided under the raisable portion (54) to touch the cam-rail slanting bucket (34) at the side thereof, and to be lifted slantingly and upward, so that the raisable portion (54) rises along the length of the horizontal portion (52) by the hinge portion provided between the horizontal portion (52) and the raisable portion (54).

The raised cap portion of the conveyor bucket (50) rotates corresponding to the advance of the conveyor bucket (50) so that the vial (AA) touches a guide rotating vial (35) as shown in FIG. 5. The guide rotating vial (35) is supported by a metal fitting (36A) of the stay (36) in the heating portion (16), although a belt can be used instead of the guide.

As shown in FIG. 3, the rail (38) disposed near the cam-rail slanting bucket (34) has a cut at a position where the vial (AA) does not support for the bottom of the vial (AA) by the rail (38) so that the vial (AA) is upward and slantingly lifted with the stands (39) and (40).

A cam-rail between the heating portion and the exit screw is configured in the opposite direction of the cam-rail (34) in FIG. 3 to return the slanted state of the vial (AA) to the horizontal state.

Because the vial (AA) is lifted slantingly and upward by the cam-rail slanting bucket (34), the vial should be returned to an initial upstanding state after being sterilized.

As above stated, plural vials (AA) sequentially conveyed can be heated to around 140° C. for 30–40 seconds to effect sterilization of the whole vial and the liquid medicine therein.

The same effect is obtained if fuel gas heating, microwave heating or the like is used as a heat source instead of the infrared line heater (17).

First, the liquid medicine is heated to a certain temperature by the infrared line heater, gas heating, microwave heating or the like in an upstanding state of the vial before being slanted, and then the heat sterilization is effected to the whole vial while being sufficiently slanted that the liquid medicine touches the inside plug.

Although FIG. 2 and FIG. 4 show the slanted conveyor bucket (50) for causing the vial (AA) to be slanted, other structures may be used for the same purpose.

While the present invention has been particularly shown and described with reference to preferred embodiments thereof, it will be understood by those skilled in the art that the foregoing and other changes in form and details can be made therein without departing from the spirit and scope of the present invention.

We claim:

1. A method for sterilizing an interior of a sealed vessel and a liquid medicine contained therein, wherein the sealed vessel has a sealing plug with an inside surface disposed in an upper neck of the sealed vessel when in a vertical orientation, comprising:

(1) moving the sealed vessel from the vertical orientation to a slanted orientation sufficiently that the liquid medicine touches the inside surface of the sealing plug;

(2) rotating the sealed vessel while in the slanted orientation; and (3) heating the sealed vessel and liquid medicine therein while the sealed vessel is being rotated in said slanted orientation to a predetermined temperature sufficiently to sterilize the interior of the sealed vessel, the liquid medicine and the inside surface of the plug.

2. The method of claim 1, wherein the sealed vessel remains at the predetermined temperature for a certain period of time after reaching.

3. The method of claim 2, wherein said sealed vessel is cooled and dried after remaining at the predetermined temperature for the certain period of time.

4. The method of claim 1, wherein a plurality of the sealed vessels are sequentially conveyed through said moving, rotating and heating steps.

5. The method of claim 4, further comprising the steps of:

measuring a temperature of the liquid medicine in each of the plurality of sealed vessels by an infrared radiation thermometer after the predetermined temperature is reached; and controlling the heating step in response to the measured temperature so as to maintain the predetermined temperature of the liquid medicine in each sealed vessel.

6. The method of claim 1, wherein the sealing plug is a rubber stopper.

7. The method of claim 1, wherein the heating step is conducted by infrared heating or fuel gas heating.

8. The method of claim 7, wherein the heating step is conducted with infrared heating.

9. An apparatus for sterilizing an interior of a sealed vessel and a liquid medicine contained therein, wherein the sealed vessel has a sealing plug with an inside surface disposed in an upper neck of the sealed vessel when oriented in a vertical orientation, comprising:

(1) conveying means for moving the sealed vessel from the vertical orientation to a slanted orientation sufficiently that the liquid medicine touches the inside surface of the sealing plug;

(2) rotating means for rotating the sealed vessel while in the slanted orientation; and (3) heating means for heating the sealed vessel and liquid medicine therein while the sealed vessel is rotating in the slanted orientation, said heating means being sufficient to heat the interior of the sealed vessel, the liquid medicine and the inside surface of the plug to cause sterilization thereof.

10. The apparatus of claim 9, further comprising:

a heat-retaining device associated with the heating means for maintaining for a certain period of time the predetermined temperature after the sealed vessel reaches the predetermined temperature.

11. The apparatus of claim 10, further comprising:

a cooling device and a drying device near the heat-retaining device to cool and dry the sealed vessel after the sealed vessel has been maintained for the certain period of time at the predetermined temperature.

12. The apparatus of claim 10, wherein the heat-retaining device is a heater.

13. The apparatus of claim 9, wherein the conveying means is a bucket conveyor.

14. The apparatus of claim 13, wherein the bucket conveyor includes a cam for moving the sealed vessel to the slanted orientation.

15. The apparatus of claim 13, wherein the the rotating means rotates the sealed vessel along an advancing direction of the bucket conveyor.

16. The apparatus of claim 9, wherein the conveying means sequentially conveys a plurality of sealed vessels through the apparatus.

17. The apparatus of claim 16, further comprising:
a control for controlling the heating means so as to maintain the predetermined temperature of liquid medicine in each of the plurality of sealed vessels in response to a temperature of each sealed vessel measured by an infrared radiation thermometer provided at an end of the heating means.

18. The apparatus of claim 9, wherein the heating means is an infrared heater.

* * * * *